United States Patent [19]

Lysaght

[11] 4,387,093

[45] Jun. 7, 1983

[54] ARTHRITIS TREATMENT

[76] Inventor: Wallace Lysaght, 9 Coniston Ave., Te Atatu South, Auckland, New Zealand

[21] Appl. No.: 332,342

[22] Filed: Dec. 18, 1981

[30] Foreign Application Priority Data

Dec. 19, 1981 [NZ] New Zealand .......................... 195881

[51] Int. Cl.³ .............................................. A61K 33/24
[52] U.S. Cl. .................................... 424/131; 424/147; 424/154; 424/156
[58] Field of Search .......................................... 424/131

[56] References Cited

U.S. PATENT DOCUMENTS

| 3,876,765 | 4/1975 | Choay | 424/105 |
| 4,007,266 | 2/1977 | Choay | 424/105 |
| 4,009,263 | 2/1977 | Shafer | 424/131 |
| 4,085,206 | 4/1978 | Rokos et al. | 424/131 |

FOREIGN PATENT DOCUMENTS 2429021 1/1980 France.

OTHER PUBLICATIONS

Chem. Abst. 86-87936g, (1977).
Chem. Abst. 86-169603v, (1977).
Merck Index, 9th Ed., (1976), pp. 311–312 and 1287–1288.

Primary Examiner—Stanley J. Friedman
Attorney, Agent, or Firm—Holman & Stern

[57] ABSTRACT

This invention relates to the treatment of arthritis by administering cobalts in a form acceptable to the body. The dosage typically comprises measured amounts of cyanocobalamin, potassium iodide, magnesium sulphate and ferrous sulphate.

40 Claims, No Drawings

ARTHRITIS TREATMENT

BACKGROUND OF THE INVENTION

This invention relates to a dietary supplement suitable for restoring the body chemistry to deal with various disorders such as arthritis, and to a method of treating such disorders.

Arthritis is a very common disease for which orthodox medical treatment is generally ineffective. It is an object of the present invention to provide a means whereby arthritis may be effectively treated.

SUMMARY OF THE INVENTION

In a first aspect the present invention consists in a method of treating a bodily disorder, the method comprising administering a non-lethal dose of a cobalt compound.

In a second aspect the present invention broadly consists in a preparation for treating a bodily disorder, said preparation comprising a non-lethal dose of a cobalt compound.

DESCRIPTION OF THE PREFERRED EMBODIMENTS

In a first preferred form of the present invention, a solution comprises 2.5 gm per 100 ml of cobalt chloride, 5 gm per 100 ml of potassium iodide, 4 gm per 100 ml of calcium carbonate and 2.5 gm per 100 ml of magnesium sulphate. Such a solution is administered to the patient suffering from arthritis, 5 ml per day for a week.

The strength and concentration of the various salts may be varied, as can the dosage given, but it is important that the dosage of cobalt salt is not lethal. It would not be safe to exceed 2.5 gm per 100 ml if the dosage is to be retained at 5 ml per day. The quantities of the other substances are not so critical however, and the cobalt can still be quite effective at much lower amounts per dose.

For example a patient may be able to accept up to 7 gm per day of potassium iodide without suffering ill effects.

If desired, ferrous sulphate or other iron compound may also be added to the solution, typically 2.5 gm per 100 ml in a solution as outlined above. However, this may be dispensed with because of the tendency of ferrous sulphate to precipitate out.

It has been found that the administration of cobalt halts the growth of the arthritis and relieves pain. The iodide salt acts to relieve stiffness and tends to bring back mobility of immobilised joints. The calcium carbonate serves as a bone strengthener and therefore it too has an important part to play in the treatment of the arthritis. It also tends to counteract nausea which may otherwise be caused by reaction of the solution with stomach acids. The magnesium sulphate acts as an anti-inflammatory agent to reduce pain, and the ferrous sulphate assists with the regeneration of red blood corpuscles.

The cobalt is the vital and most important feature of the mixture, although the addition of the iodide and the calcium is nearly as important. The other substances are purely optional.

In a second preferred form a single 5 ml dose comprises 300 micrograms of cyanocobalamin, 5% by weight potassium iodide, and 5% by weight calcium carbonate. Such a mixture has a bitter taste, however, and it may therefore be desirable also to add flavourings, typically in the form of 5% by weight concentrated syrup and 2½% by weight of concentrated peppermint water. The preparation is preferably made up using deionized water.

Again, all of these quantities are variable, and the quantity of cyanocobalamin per dose can be varied quite considerably. This formulation still incorporates cobalt and iodine in forms acceptable to the human body. In many circumstances the use of cyanocobalamin is preferable to cobalt chloride, as the cobalt chloride can sometimes produce a feeling of nausea. However, the hydrochloric acid produced by the digestive system tends to destroy the cyanocobalamin, and so calcium carbonate is used to allow a greater absorption by the body of the cyanocobalamin. Other alkaline substances may be used to achieve the same result. However, calcium is preferred because of its ability to be incorporated into the bones. The most beneficial time for taking a dose of the preparation is about half an hour before a meal, when stomach acid flow is virtually zero.

Instead of being administered in aqueous form, the present invention may be applied in tablet or capsule form. A typical tablet or capsule, to be taken once a day, may comprise approximately 125 milligrams of cobalt chloride, approximately 250 milligrams of potassium iodide, approximately 200 milligrams of calcium carbonate, approximately 125 milligrams of magnesium sulphate and approximately 125 milligrams of ferrous sulphate. Other materials may be added as required for taste or bulk and/or for any other purpose (such as vitamins etc). Again, the quantities of the various compounds are variable, and some of them may be omitted, but the cobalt is essential and should not be much more than 125 milligrams per dose. Smaller dosages of cobalt may also be effective against arthritis, but may in some circumstances take a longer time to work. Again, cyanocobalamin or some other cobalt compound may be used in place of cobalt chloride.

If it is desired that the tablets be administered more often than once per day, then the quantities of the ingredients should be reduced accordingly.

Osteo arthritis is a form of arthritis having a very predictable pattern in response to treatment by the present invention, and in the great majority of cases where the present invention is used the sufferers find that within two or three doses an increase in the level of pain occurs. This typically lasts from three to four days and then a complete remission lasting two or three weeks or longer occurs. A relapse then follows, sometimes for as long as a few days, but of much less severity than before treatment started. This pattern recurs, with the relapses becoming shorter and less severe until a complete remission is obtained. Once this has been achieved a continued single dose twice per month is generally sufficient to prevent the condition from returning.

Rheumatoid arthritis also tends to increase in pain after two or three doses of the preparation. This also may last three to four days. Then there is typically a remission of a few days, then a relapse for another few days. This pattern recurs for quite some time although again the severity of the relapses gradually decreases. Again, once a complete remission has been obtained, a continued dosage twice per month is advisable, and sufficient to keep the disease at bay.

Psoriasis is allied to arthritis and also reacts favourably to treatment by the present invention. Less severe cases tend to respond relatively quickly without any apparent discomfort. However, severe cases of psoriasis can become quite painful with a burning sensation and the shedding of dry scaly skin, which then leaves a new skin beneath.

Anaemia has also been found to respond well to the present invention. Typically, a normal red corpuscle count is reached within two or three weeks of continued treatment.

Many other variations to the above may also be made without departing from the scope of the present invention as broadly defined or envisaged. For example, the various components may be administered separately rather than together in a single dose, although it is still preferred that they be administered at the same time.

The treatment may be applied to humans or animals, although the dosages for animals will vary in accordance with the size and type of the animal.

I claim:

1. A method for treating arthritis, comprising orally administering to the affected subject a non-lethal, therapeutic dosage of a preparation consisting essentially of a cobalt compound.

2. A method as claimed in claim 1 wherein the preparation is administered in aqueous form.

3. A method as claimed in claim 1 wherein the aqueous preparation contains approximately 6 mg cyanocobalamin per 100 ml.

4. A method as claimed in claim 1 wherein the aqueous preparation contains up to 2.5 grams of cobalt chloride per 100 milliliters.

5. A method as claimed in claim 1 wherein the aqueous preparation further contains about 5 grams of potassium iodide per 100 milliliters.

6. A method as claimed in claim 2 wherein the preparation further contains about 4 grams of calcium carbonate per 100 milliliters.

7. A method as claimed in claim 2 wherein the preparation further contains approximately 2.5 grams per 100 milliliters of magnesium sulphate.

8. A method as claimed in claim 4 wherein the method comprises administering 5 milliliters of the aqueous preparation a day.

9. A method as claimed in claim 1 wherein the preparation is administered in tablet or capsule form.

10. A method as claimed in claim 9 wherein a single tablet or capsule comprises between 0.3 and 125 milligrams of the cobalt compound, approximately 250 milligrams of potassium iodide, approximately 200 milligrams of calcium carbonate, approximately 125 milligrams of magnesium sulphate and approximately 125 milligrams of ferrous sulphate.

11. A method as claimed in claim 10 wherein the method comprises orally administering one tablet or capsule per day.

12. The method of claim 1, wherein the compound is cobalt chloride.

13. The method of claim 1, wherein the cobalt compound is administered in combination with an iodine compound in an amount sufficient to alleviate stiffness and promote mobility of affected joints.

14. The method of claim 1 or 13, wherein the cobalt compound, or cobalt and iodine compounds, are administered in combination with a calcium compound in an amount sufficient to counteract deterioration of bone tissues.

15. The method of claim 1, wherein the cobalt compound is cyanocobalamin.

16. The method of claim 15, wherein the cyanocobalamin is administered in combination with an alkaline substance in an amount sufficient to protect the cyanocobalamin from destruction by digestive acids before it can be utilized by the body.

17. The method of claim 16, wherein the alkaline substance is a calcium compound.

18. The method of claim 17, wherein the calcium compound is calcium carbonate.

19. The method of claim 13, wherein the iodine compound is an iodide.

20. The method of claim 19, wherein the iodide is potassium iodide.

21. The method of claim 1, wherein the cobalt compound is administered in combination with (a) an iodine compound in an amount sufficient to alleviate stiffness and promote mobility of affected joints, (b) a calcium compound in an amount sufficient to counteract deterioration of affected bone tissue, (c) a magnesium compound in an amount sufficient to counteract inflammation, and (d) an iron compound in an amount sufficient to promote regeneration of red blood cells.

22. The method of claim 21, wherein the cobalt compound is cobalt chloride or cyanocobalamin, the iodine compound is potassium iodide, the calcium compound is calcium carbonate, the magnesium compound is magnesium sulfate, and the iron compound is ferrous sulphate.

23. A method for treating psoriasis comprising orally administering to the affected subject a non-lethal therapeutic dosage of a preparation consisting essentially of a cobalt compound.

24. The method of claim 23, wherein the compound is cobalt chloride.

25. The method of claim 23, wherein the cobalt compound is cyanocobalamin.

26. The method of claim 25, wherein the cyanocobalamin is administered in combination with an alkaline substance in an amount sufficient to protect the cyanocobalamin from destruction by digestive acids before it can be utilized by the body.

27. The method of claim 26, wherein the alkaline substance is a calcium compound.

28. The method of claim 27, wherein the calcium compound is calcium carbonate.

29. The method of claim 1, wherein the arthritis to be treated is rheumatoid arthritis.

30. The method of claim 1, wherein the arthritis to be treated is osteoarthritis.

31. A preparation for the treatment of arthritis and psoriasis adapted for the oral administration of a cobalt compound consisting essentially of a non-lethal therapeutic dosage of a cobalt compound and calcium carbonate in an amount sufficient to protect the cobalt compound from destruction by digestive acids and permit adsorption of the cobalt compound by the body.

32. A preparation as claimed in claim 31 further comprising an iodine compound.

33. A preparation as claimed in claim 32 wherein the iodine compound is potassium iodide.

34. A preparation as claimed in claim 31 further comprising a magnesium salt.

35. A preparation as claimed in claim 34 wherein the magnesium salt is magnesium sulphate.

36. A preparation as claimed in claim 31 further comprising ferrous sulphate.

37. The preparation of claim 36, comprising an aqueous solution containing about 25 gm FeSO$_4$ per 100 ml of solution.

38. The preparation of claim 31, wherein the cobalt compound is cyanocobalamin.

39. The invention of claim 31, wherein the preparation is a tablet or capsule and the cobalt compound is present in an amount from about 0.3 to 125 mg.

40. The invention of claim 39, wherein the preparation further includes approximately 125 milligrams of the cobalt compound, approximately 250 milligrams of potassium iodide, approximately 200 milligrams of calcium carbonate, approximately 125 milligrams of magnesium sulphate, and approximately 125 milligrams of ferrous sulphate.

* * * * *